United States Patent [19]

Zanzucchi et al.

[11] 4,399,361

[45] Aug. 16, 1983

[54] DEVICE FOR MULTISAMPLE INFRARED ANALYSIS OF MATERIALS IN MICROGRAM QUANTITY

[75] Inventors: Peter J. Zanzucchi, Lawrenceville; William R. Frenchu, Princeton, both of N.J.

[73] Assignee: RCA Corporation, New York, N.Y.

[21] Appl. No.: 268,283

[22] Filed: May 29, 1981

[51] Int. Cl.³ .......................................... G01N 21/26
[52] U.S. Cl. .................................. 250/343; 250/341; 250/358.1
[58] Field of Search ..................... 250/341, 343, 358.1, 250/359.1; 356/51, 432, 440, 244

[56] References Cited

PUBLICATIONS

"Infrared Microsampling in Bio-Medical Investigations," by W. B. Mason, at The Pittsburgh Conf. on Analytical Chem. and Appl. Spectroscopy, Mar. 1958, pp. 1-11.
"The Perkin-Elmer Infrared Accessories Catalog," The Perkin-Elmer Corporation, 1970, pp. 1, 4-5, 40-46, and 98, only.

*Primary Examiner*—Davis L. Willis
*Attorney, Agent, or Firm*—Birgit E. Morris; Donald S. Cohen; Joseph D. Lazar

[57] ABSTRACT

A sampling device adapted for mounting on a conventional microsampling apparatus for infrared spectroscopy is arranged to sample a plurality of different samples of unknown material during one operation. The device supports by a clamp an IR-transparent substrate on which solutions of samples are deposited. After evaporation of the solvent, the residue of unknown material is analyzed by conventional spectroscopy procedures. Each of the plurality of such samples deposited on the substrate are manually rotated into and out of exposure to the IR beam of the apparatus for rapid analysis.

8 Claims, 3 Drawing Figures

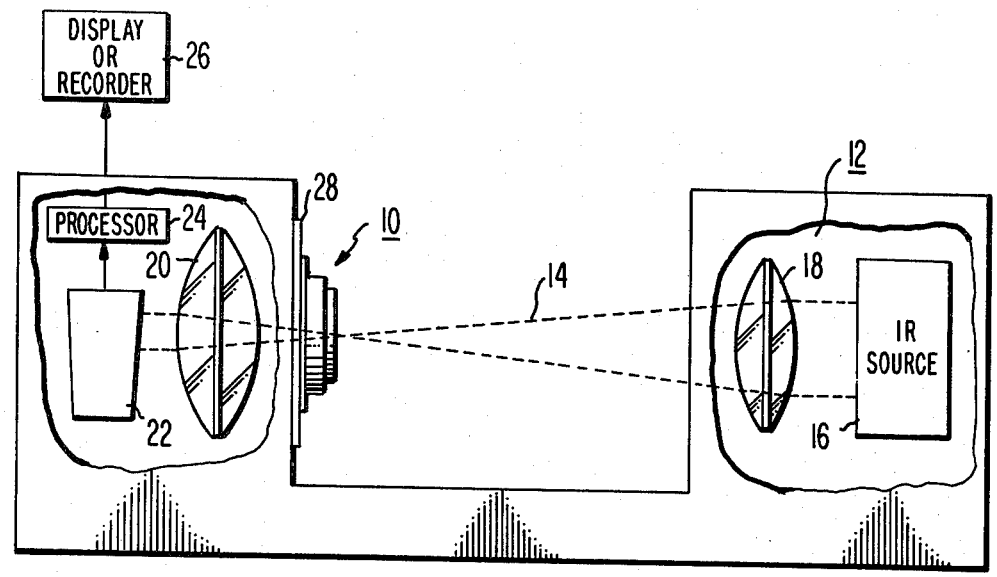
Fig. 1
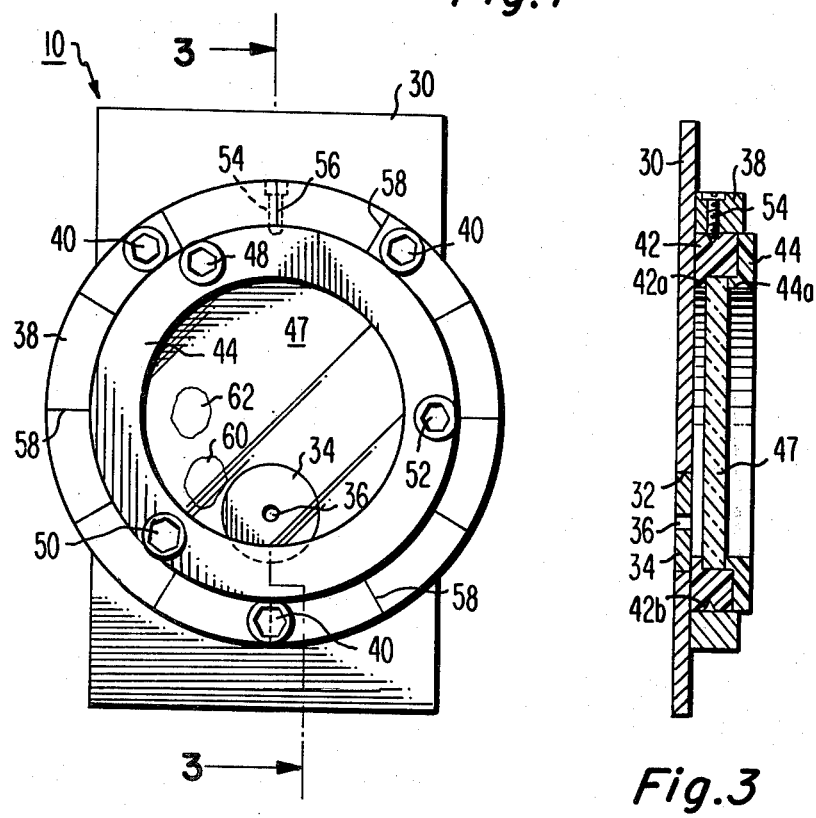
Fig. 2
Fig. 3

DEVICE FOR MULTISAMPLE INFRARED ANALYSIS OF MATERIALS IN MICROGRAM QUANTITY

This invention relates to the identification of materials in microgram quantity by IR spectroscopy.

BACKGROUND OF THE INVENTION

Small amounts of contaminants, typically in microgram quantities, when found on the surface of an electronic device, need often to be identified to determine the origin of the unwanted material. Devices for supporting small quantities of samples for infrared analysis are available and are well-known in the art. See the paper "Infrared Microsampling in Bio-Medical Investigations," by W. B. Mason, presented at The Pittsburgh Conference on Analytical Chemistry and Applied Spectroscopy, March, 1958, pp. 1-11. A typical commercial apparatus for infrared spectroscopy is a Perkin-Elmer Spectrophotometer. Such apparatus are usually provided with support mechanisms or accessories arranged to support one sample at a time. Preparing one sample at a time or preparing a plurality of samples on a number of separate discs or support devices as is done in such apparatus is a slow and time consuming process. Moreover, since the sampling procedure is spread over a considerable period of time, the possibility of contaminating the sample and the sample accessory equipment is increased. There is a need in the art for a single device or accessory for use in infrared spectrophotometers that will support at one time a number of samples of microgram quantity.

SUMMARY OF THE INVENTION

According to this invention, an accessory device is provided for use with an IR microsampling apparatus, such as an infrared spectrophotometer, to support an IR-transparent substrate for receiving samples of materials at several substrate locations. The substrate is moveable to position in sequence each sample in the IR beam of the apparatus.

BRIEF DESCRIPTION OF THE DRAWING

In the drawing:

FIG. 1 is a simplified schematic of the device of the invention in the environment of a conventional IR spectrophotometer;

FIG. 2 is a front elevation view of the device of the invention; and

FIG. 3 is a side view, in section, of the device shown in FIG. 2.

DETAILED DESCRIPTION OF A PREFERRED EMBODIMENT

The sampling accessory device 10 of the invention is shown in FIG. 1 in operative position within an infrared (IR) spectroscopy apparatus 12. The apparatus 12 provides an infrared beam 14 of electromagnetic energy in the infrared spectrum from an infrared source 16 of the apparatus 12. The apparatus 12 further includes a first lens 18 for focusing the IR beam 14 at the device 10 and a second lens 20 for collecting the beam passing through the device 10. A detecting apparatus 22 responds to the beam passed through the device 10 to generate an electrical signal representing the information contained in the beam. The signal from the detected light is coupled to a processor 24 to process the infrared beam information derived from the device 10. Processor 24 applies the processed information in suitable signal format to a recorder or display 26 for real time or storage use. The apparatus 12 is of conventional form and may be of the type such as a Perkin-Elmer Infrared Spectrophotometer with microcondensor (microsampling) optics as shown. The apparatus 12 is provided with an accessory support bracket 28 suitably positioned on the housing of apparatus 12 in such a position as to support a sampling accessory in the beam 14 substantially at the focal point thereof. The device 10 of the present invention is arranged to be mounted in such a bracket 28 and thereby be positioned at the focal point of the IR beam 14 for infrared spectroscopy.

The device 10 of the invention is shown in FIGS. 2 and 3 to which reference is now made. The base plate 30 formed of a metal such as steel is adapted to be slid into bracket 28 for mounting against a vertical wall of the apparatus 12. Base plate 30 has an aperture 32 into which is fitted a metallic disc 34 suitably made of aluminum. In the center of aluminum disc 34 is provided an aperture 36 having an outside diameter of about 1.6 millimeters (1/16"). Aperture 36 serves as the IR-beam path for the device as will be further explained. The aperture (36) dimension is chosen to be sufficiently large to provide a reasonable signal-to-noise ratio (S/N) but small enough to insure that only IR-radiance which has passed through the sample material is transferred through to the detecting means of the spectrophotometer 12.

A brass ring 38 is mounted on the plate 30 with three screws 40, typically Allen-head screws, suitably positioned about the ring 38 to affix the ring 38 securely to the plate 30. A pair of rings 42 and 44 made of plastic material, preferably a carbon tetrafluoride polymer $(CFl_4)_n$, commonly available as the trademarked material known as Teflon, is used to hold a substrate for receiving the sample material to be analyzed. The first Teflon ring 42 has a shoulder portion 42a to receive a disc serving as a substrate 47 formed of a salt such as silver bromide (AgBr) or silver chloride (AgCl). The substrate 47 is about 1 millimeter in thickness and about 25 millimeters in outside diameter. In preferred form, the substrate 47 is formed of silver chloride. The substrate 47 must be transparent in infrared radiation in order to pass the IR irradiance through the material that will be mounted on the substrate 47. Moreover, the substrate 47 must be inert with respect to the liquids that are used to carry the sample material in solution form for deposition on the plate. It is important for plastic ring 42 to be inert to the salt forming the substrate 47 and should furthermore be inert to common metals such as aluminum or stainless steel.

A second Teflon ring 44 is disposed over the first ring 42 and is provided with an extension member 44a to press against the substrate 47 to hold it in clamped position between the two rings 42 and 44. Three screws 48, 50 and 52, preferably with Allen-heads, are used to secure the two rings 42 and 44 together. They are preferably spaced equally on the periphery of the rings so that each one is spaced from the other by 120°. One of the screws, such as screw 48, is made different in appearance than the other two screws 50 and 52, as by a colored head or a knurled head, to serve as the reference location for the assembly as it is rotated relative to a starting position as will be further described.

The inner or bottom Teflon ring 42 is provided with a V-groove 42b for receiving a screw 54 passing through the brass ring 38 to hold the Teflon ring assembly in position. The Teflon ring assembly, when clamped together carrying the substrate 47, will freely rotate within brass ring 38 by cooperation of screw 54 sliding within the V-groove 42b without being released from attachment to the plate 30. A reference mark or line 56 is provided on the brass ring 38 and suitably positioned along a vertical axis of the assembly for initial reference position. Additional index marks 58 are spaced every 30° about the ring 36, thereby providing a total of twelve, spaced, reference marks.

In operation, samples of material that are to be analyzed are dissolved in an organic solvent such as methylene chloride, acetone or heptane or indeed water if the material is soluble in water. The samples are transferred to the surface of substrate 47 by a syringe of predetermined volume such as a 10 microliter syringe. The material in solution form is deposited on the substrate 47 in a position that will be in register over the aperture 36 when the substrate is rotated thereover. Several specimen samples are shown in drawing FIG. 2 represented by reference numerals 60 and 62. As successive drops of the solvent evaporate, the non-volatile sample material is left on the substrate 47 surface. Care must be taken that these drops of solvent are deposited on the surface slowly to avoid spreading the sample in solution form on the substrate 47 beyond the region defined by the aperture 36.

The several samples 60 and 62 are shown on the drawing, were obtained by dissolving a sample in 10 microliters of methylene chloride. It should be appreciated that this procedure works best when a very volatile solvent is used. The rate of solvent evaporation can be increased by directing a jet of dry nitrogen gas towards the sample deposition region. For the less volatile solvents, heat may be applied to speed-up the evaporation by using either an infrared lamp or a hot plate. All of these techniques to expedite the solvent evaporation rate are well known in the art.

Care should be taken while depositing the solute on the substrate 47 to prevent scratching of the substrate surface. Since a substrate formed of silver chloride has a relatively high refractive index, an excessive number of scratches will reduce the light transmittance from the beam 14, thereby reducing the accuracy of the measurements being made.

The method carried out using the apparatus of the invention would be a quantitative analysis if the amount of material sampled was known. One important reason that this procedure does not provide for a precise quantitative analysis is that the samples 60 and 62 are not always uniform in thickness. Accordingly, the reduction in thickness uniformity does not allow the invention to be used for precise quantitative analyses.

As indicated above, solvents with a low volatility or a large heat of vaporization, such as water, are difficult to use because they do not evaporate quickly. Ideally, all components of the sample of material to be evaluated, contacted by the solvent of choice, should be equally soluble or the solvent will preferentially extract select components. This preferential solubility can lead to errors in determining the relative composition of small samples. Nevertheless, by use of appropriate solvents, this sort of problem can be minimized.

While it is preferred that in practicing the invention the material to be sampled is dissolved, the device of the invention allows for a great deal of flexibility in sampling unknown materials. For example, the invention is particularly useful for sampling small amounts of material ordinarily very difficult to work with by infrared analysis. A solder flux, for example, used at the connections of transistors can be appraised by this device by placing the solder flux in a solution of methanol.

While the use of the invention has been described in terms of microsampling solid materials, it will be appreciated by those skilled in the art that liquids may be also used provided that they are viscous enough to not flow or spread across the surface of the substrate 47. Examples of such viscous liquids will include high molecular weight oils, low molecular weight polymers and other viscous materials that are generally used in the electronic industry.

In the practice of the invention, as many as 12 different samples can be deposited on the substrate 47 and processed by the infrared spectrophotometer exposing each of the 12 samples in sequence by manual rotation of the rings 42 and 44. It is desirable to rotate the Teflon rings 42 and 44 in one direction such as a counter-clockwise direction, from the initial position identified by the reference mark 56 in coincident position with the first screw 48. In this way the samples can be identified and correlated relative to each other. For example, 12 samples taken from 12 different portions of a device that has some unknown purities can be sampled and properly correlated.

What is claimed is:
1. In a microsampling apparatus for infrared (IR) spectroscopy of the type having means for providing an IR beam to indicate a sample of material, optical means for focusing said beam on said sample, and means for subsequently processing the IR beam to provide information representing the ingredients of the material, wherein the improvement comprises:
   a base plate mounted at the focal point of said beam and an aperture in said plate for passing said IR beam; and
   means attached to said base plate for supporting a moveable IR-transparent substrate;
   said substrate arranged to receive one or more samples of material at locations on said substrate moveable to an optical register position over said aperture to pass said beam.
2. The apparatus of claim 1, wherein said material is solid residue from an evaporable solvent solution.
3. The apparatus of claim 1, wherein said material is a viscous liquid.
4. The apparatus of claim 1, wherein said substrate is formed of an IR-transparent salt.
5. The apparatus of claim 4, wherein said salt is silver chloride (AgCl).
6. The apparatus of claim 4, wherein said salt is silver bromide (AgBr).
7. The apparatus of claim 1, wherein said substrate support is a pair of mating rings formed of a plastic polymer for supporting the substrate in a fixed, clamped position therebetween, said ring holding said substrate being arranged for rotation over said base plate.
8. The apparatus of claim 7, wherein said rings are rotatable within a metallic ring, said metallic ring having indicia means to determine the location of material on said substrate relative to a reference location.

* * * * *